(12) United States Patent
Breguet

(10) Patent No.: US 9,724,174 B2
(45) Date of Patent: Aug. 8, 2017

(54) ENDODONTIC INSTRUMENT FOR DRILLING ROOT CANALS

(71) Applicant: FKG DENTAIRE S.A., La Chaux-de-Fonds (CH)

(72) Inventor: Olivier Breguet, Le Locle (CH)

(73) Assignee: FKG Dentaire S.A., La Chaux-de-Fonds (CH)

( * ) Notice: Subject to any disclaimer, the term of this patent is extended or adjusted under 35 U.S.C. 154(b) by 0 days.

(21) Appl. No.: 14/408,341

(22) PCT Filed: Jun. 25, 2013

(86) PCT No.: PCT/CH2013/000113
§ 371 (c)(1),
(2) Date: Mar. 11, 2015

(87) PCT Pub. No.: WO2014/000116
PCT Pub. Date: Jan. 3, 2014

(65) Prior Publication Data
US 2015/0313686 A1    Nov. 5, 2015

(30) Foreign Application Priority Data
Jun. 26, 2012   (CH) .......................................... 898/12

(51) Int. Cl.
*A61C 5/02* (2006.01)
*A61B 17/16* (2006.01)
*A61C 5/42* (2017.01)

(52) U.S. Cl.
CPC .......... *A61C 5/023* (2013.01); *A61B 17/1615* (2013.01); *A61C 5/42* (2017.02)

(58) Field of Classification Search
CPC ............................ A61C 5/023; A61B 17/1615
(Continued)

(56) References Cited

U.S. PATENT DOCUMENTS 5,876,202 A * 3/1999 Berlin ...................... A61C 3/02
                                                            408/230
6,074,209 A * 6/2000 Johnson ................ A61C 5/025
                                                            433/102
(Continued)

FOREIGN PATENT DOCUMENTS

CH    692 484 A5    7/2002
FR    2 821 000 A1  8/2002
JP    S59 019120 U  2/1984

OTHER PUBLICATIONS

International Search Report Corresponding to PCT/CH2013/000113 mailed Oct. 4, 2013.

*Primary Examiner* — Cris L Rodriguez
*Assistant Examiner* — Mirayda A Aponte
(74) *Attorney, Agent, or Firm* — Davis & Bujold PLLC; Michael J. Bujold

(57) ABSTRACT

An endodontic instrument (20) for drilling root a canal within a tooth. The instrument has a working area (21) that is arranged so as to form, shape and/or cut the inner wall of the root canal. The instrument has a plurality of flutes wound around a central axis in the form of a spiral, within a conical envelope (25) so as to have a cross-section that becomes narrower from a first end (23) to the second end (26) of the instrument. The working area (21) is sub-divided into adjacent segments (13) such that the flutes alternately have a straight section and a section that is twisted in the form of a spiral and are arranged, in such a way, that the edges of the flutes are located either on the conical envelope (25) or inside the envelope on the straight sections or on the twisted sections.

6 Claims, 4 Drawing Sheets

(58) Field of Classification Search
USPC .......................................................... 433/102
See application file for complete search history.

(56) References Cited

U.S. PATENT DOCUMENTS 7,125,252 B2   10/2006   Rouiller et al.
2007/0026360 A1   2/2007   Buchanan \* cited by examiner

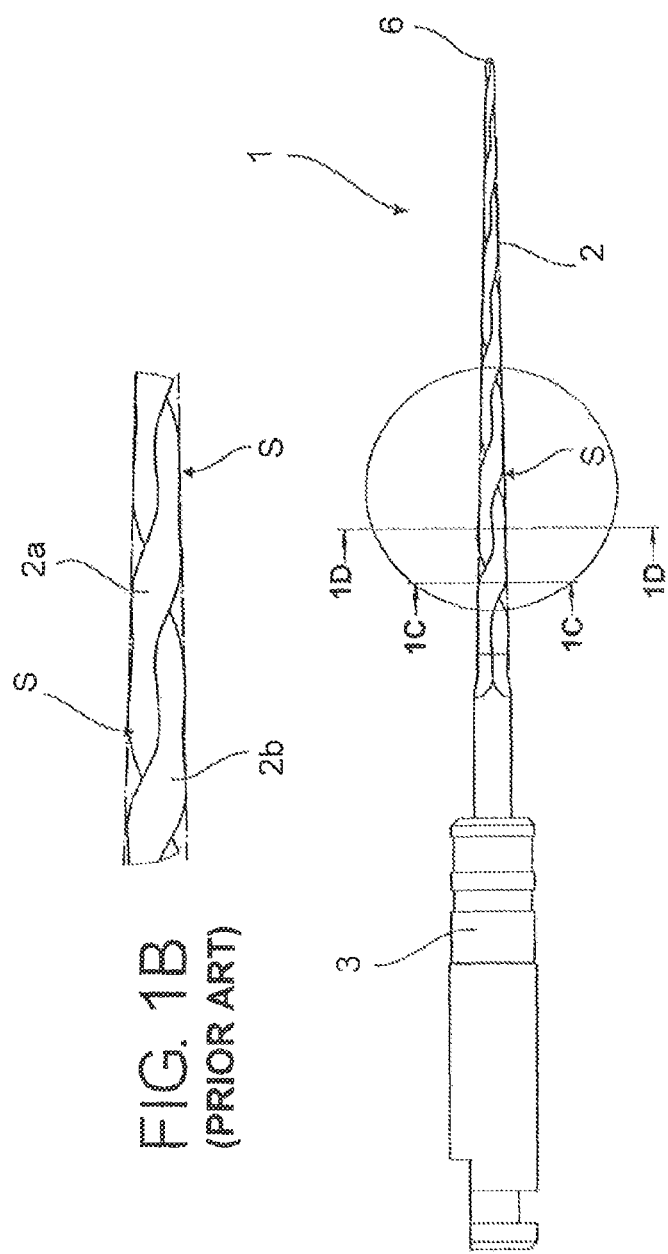

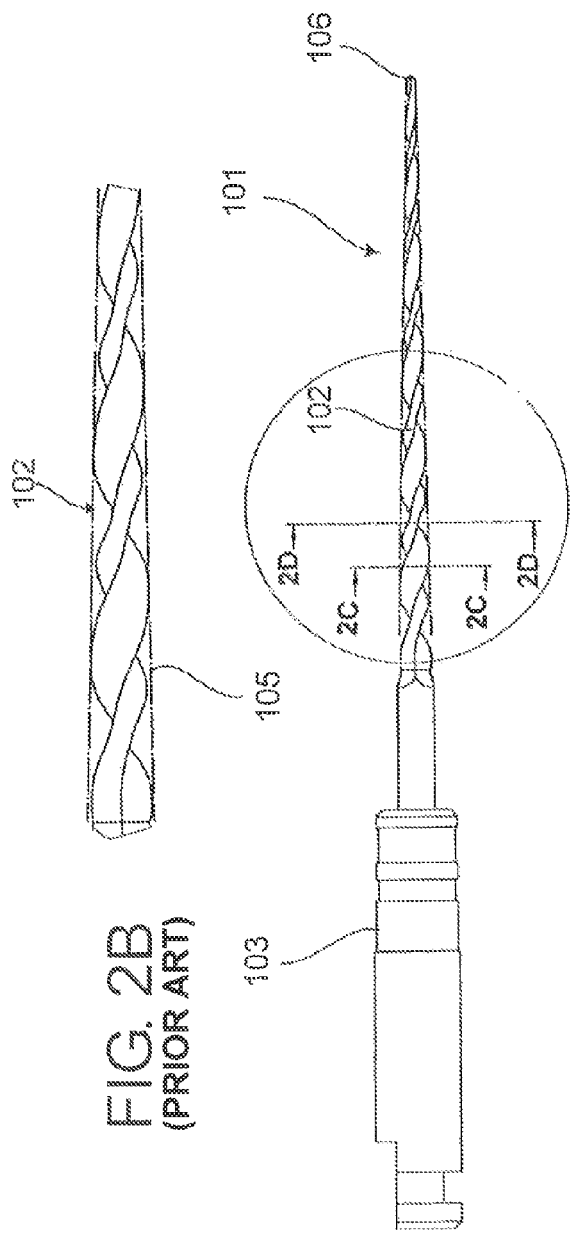
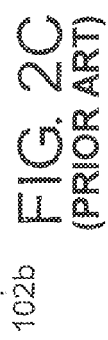
FIG. 2A (PRIOR ART)
FIG. 2B (PRIOR ART)
FIG. 2C (PRIOR ART)
FIG. 2D (PRIOR ART)

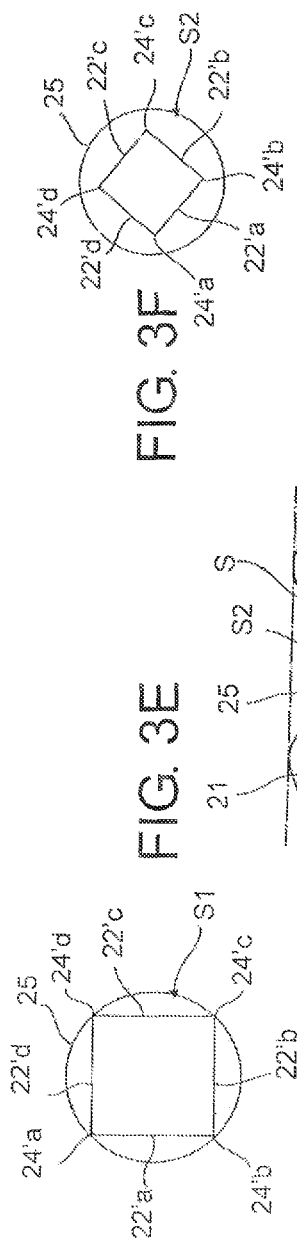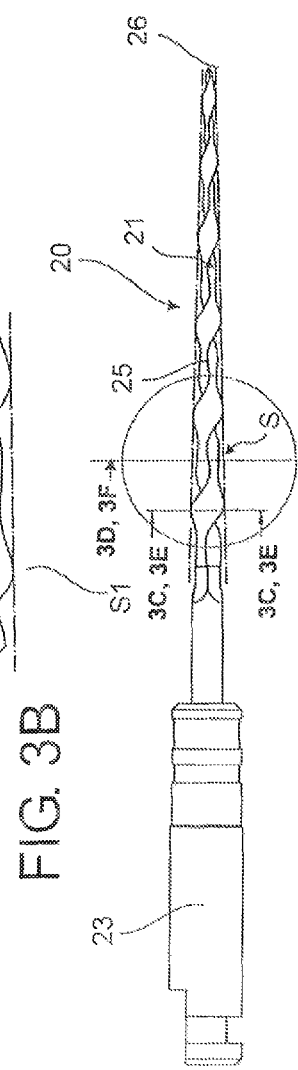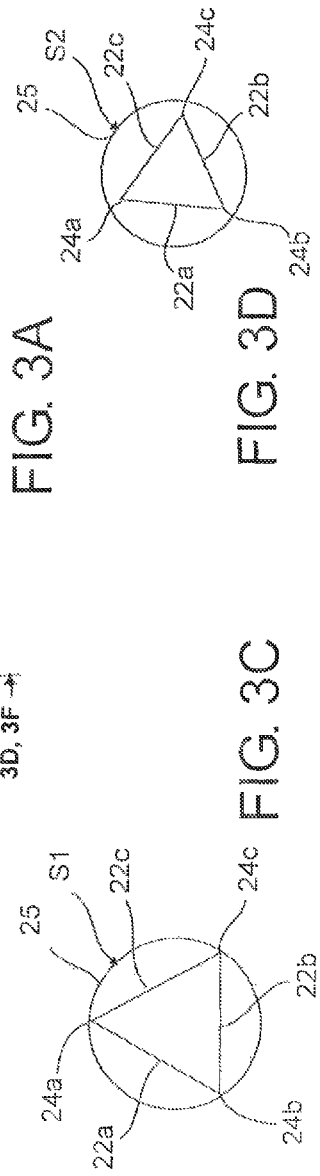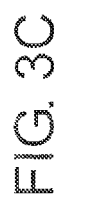

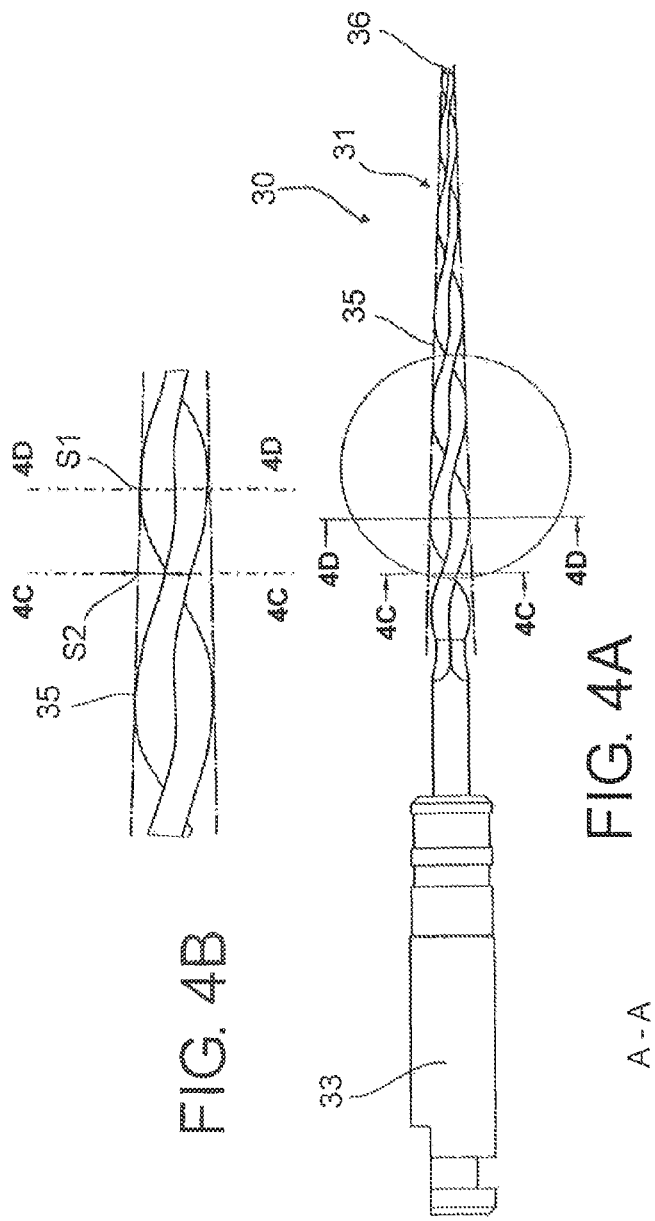
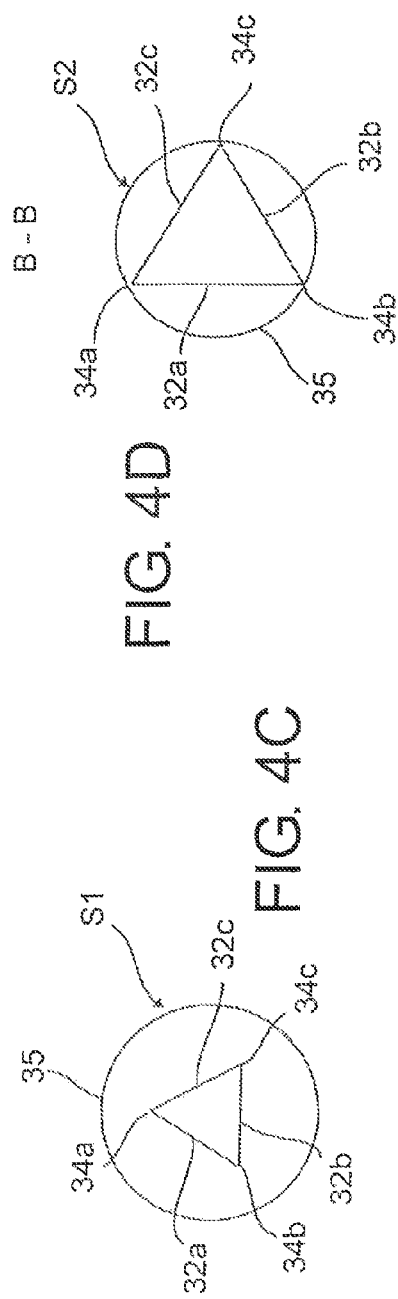

ENDODONTIC INSTRUMENT FOR DRILLING ROOT CANALS

This application is a National Stage completion of PCT/CH2013/000113 filed Jun. 25, 2013, which claims priority from Swiss patent application serial no. 898/12 filed Jun. 26, 2012.

FIELD OF THE INVENTION

The present invention concerns an endodontic instrument for drilling a patient's tooth, specifically an instrument for drilling root canals, the instrument having a longitudinal axis and comprising a working area that corresponds to a first extremity called the free end of the instrument, the purpose of the working area being to form and/or shape and/or cut the interior wall of the root canal, with the working area being connected to a support tip designed for attachment to a support corresponding to a second extremity of the instrument.

BACKGROUND OF THE INVENTION

Cleaning and shaping root canals of a tooth to prepare it for receiving filling substances is accomplished with the use of drilling instruments having one active portion, called the working portion, the purpose of which is to form, cut and clean the interior walls of the root canal to prepare it for receiving treatment materials and filling material in order to prevent any contact with oxygen that might cause the development of bacteria within the tooth.

Most instruments for drilling root canals comprise an active portion called the cutting portion with a conical envelope and one or more cutting edges wound in a spiral along the active portion.

The spiral shape of the instrument is crucial for evacuating dental debris towards the outside of the root canal. During use, the conical portion of the instrument, which is the working portion, may undergo a phenomenon whereby the material removed from the canal along the spiral becomes wrapped around the instrument, forming a covering that renders the instrument completely useless. In addition, when this instrument is introduced into the canal and rotated using the hand piece equipped with an electric motor, it may become embedded inside the canal, which leads to blockage and may cause it to break.

For this reason it is recommended that this type of instrument be used only with a back-and forth motion, possibly rotating it slightly and alternating in one direction and the opposite direction, to prevent it from becoming stuck and incurring the distinct risk of breakage, which can be catastrophic due to the difficulties of extracting a fragment of a broken instrument.

Several instruments have been developed to overcome these difficulties. For example, one notable endodontic instrument is cited in Swiss Patent 692 484, which is designed specifically to eliminate, at least partially, the embedding effect by varying the spiral angle of the flutes on the active portion, called the working area of the instrument. Another instrument described in French Patent No. 01 02452 also at least partially prevents this embedding effect due to undulation of the flutes on the active portion of the instrument.

Japanese Publication JP 59 019120 describes an instrument that comprises a working area having adjacent straight segments that alternate with twisted segments. However, these segments are uniform in length, and the flutes do not penetrate inside the conical envelope. Furthermore, the transverse sections of the instrument in the working area do not comprise variations that are useful for both the functions of "cutting the material in the canal wall" and "evacuating the cut material along this wall."

These two instruments are effective to a certain extent insofar as the desired non-embedding is concerned. However, none of these known instruments can guarantee that embedding absolutely will not occur during use by a practitioner.

Another quality that a good endodontic instrument must possess is cutting efficiency. This property allows dental work to take place without excessive heating or smoothing of the canal walls and thus plugging the tubules of the root canal with infected debris. Efficient cutting also means the instrument works with fewer torsion constraints, which reduces the risk of instrument breakage during use. Moreover, efficient cutting allows the operator to proceed with a lower working torque, leading to increased patient safety if there is breakage during torsion. Finally, efficient cutting allows the root to be treated more quickly, eliminating excessive cyclic fatigue as the instrument follows the root canal curves during functioning.

Conversely, cutting capacity that is too great may lead to a high risk of embedding, which is obviously an undesirable effect and imperative to avoid because of the risk of breakage. Because of this, it is essential when shaping the active portion, called the working area, to strike a compromise between efficient cutting and efficient anti-embedding operations.

SUMMARY OF THE INVENTION

The present invention proposes to achieve such an instrument that is responsive to these two somewhat antithetical exigencies while still retaining efficient cutting and anti-embedding functions, by placing reliable tools at the disposal of professionals to allow them to execute the required tasks while ensuring the patient's safety.

This objective is attained by the endodontic instrument for drilling root canals according to the invention, as defined in the preamble and characterized in that the flutes are integrally located on and inside a conical envelope that becomes progressively more narrow from the second extremity to the first extremity of the instrument, and in that the working area is subdivided into adjacent segments in which the sections of alternate flutes are either straight or twisted spirals, and which are disposed in such a way that their edges are located either on the conical envelope or inside the conical envelope at the level of the straight sections and at the level of the twisted sections.

According to a first embodiment of the instrument, the edge of each corresponding flute on the straight section is located on the conical envelope and the edge of each corresponding flute of the twisted section is located inside the conical envelope.

According to a second embodiment, the edge of each corresponding flute on the straight section is located inside the conical envelope and the edge of each corresponding flute on the twisted section is located on the conical envelope.

In every embodiment, the working area of the instrument comprises at least two flutes.

In the first embodiment of the instrument, for each of the segments, the transverse section on the working area at the level of the straight section has a surface that is higher than the transverse section of the working area at the level of the adjacent twisted section.

In the second embodiment of the instrument, for each of the segments, the transverse section of the working area at the level of the straight surface has a lower surface than the transverse section of the working area at the level of the adjacent twisted section.

In both embodiments, for each of the segments, the transverse section on the working area at the level of the straight section and at the level of the twisted section may be shaped like an equilateral triangle centered on the central axis or a square centered on the central axis.

The number of segments on the instrument advantageously ranges from one to five.

The transverse section of the instrument in the portions where the edges are located on the conical envelope and the portions where the edges are located inside the conical envelope has a surface difference ranging from 5 to 50%.

BRIEF DESCRIPTION OF THE DRAWINGS

The present invention and its advantages will be better understood from reading the following detailed description of preferred embodiments of the invention, with reference to the attached drawings given by way of non-limiting examples, in which:

FIG. 1A represents a prior art instrument as defined in Swiss Patent No. 692 484;

FIG. 1B is a close up view of a portion of the prior art instrument as shown in FIG. 1A;

FIG. 1C is a sectional view of the prior art instrument along section line 1C-1C as shown in FIG 1A;

FIG. 1D is a sectional view of the prior art instrument along section line 1D-1D as shown in FIG. 1A;

FIG. 2A represents a prior art instrument as defined in French Patent No. 01 02452;

FIG. 2B is a close up view of a portion of the prior art instrument as shown in FIG. 2A;

FIG. 2C is a sectional view of the prior art instrument along section line 2C-2C as shown in FIG. 2A;

FIG. 2D is a sectional view of the prior art instrument along section line 2D-2D as shown in FIG. 2A;

FIG. 3A is a plane view illustrating the instrument of the invention with its area known as the working area and its supporting tip;

FIG. 3B is a partially enlarged view of the working area of the instrument of FIG. 3A;

FIG. 3C is a transverse cross-sections taken along line 3C-3C illustrated in FIG. 3A in a first embodiment of the instrument;

FIG. 3D is a transverse cross-section taken along line 3D-3D illustrated in FIG. 3A in a first embodiment of the instrument;

FIG. 3E is a transverse cross-sections taken along line 3E-3E illustrated in FIG. 3A in a variation of the embodiment of the instrument in FIG. 3A;

FIG. 3F is a transverse cross-section taken along line 3F-3F illustrated In FIG. 3A in a variation of the embodiment of the instrument in FIG. 3A;

FIG. 4A is a plane view illustrating a second embodiment of the instrument of the invention;

FIG. 4B is a partially enlarged view of the working area of FIG. 4A; and

FIG. 4C is a transverse cross-sections taken along line 4C-4C illustrated in FIGS. 4A and 4B;

FIG. 4D is a transverse cross-section taken along line 4D-4D illustrated in FIGS. 4A and 4B.

DETAILED DESCRIPTION OF THE PREFERRED EMBODIMENTS

With reference to FIGS. 1A, 1B, 1C and 1D, instrument 1 such as the one shown for drilling root canals in a patient's tooth, which corresponds to the prior art defined in Swiss Patent No. 692 484, comprises a working area 2 designed to form and/or shape and/or cut the interior wall of a root canal, the working area being equipped with a supporting tip 3 designed for attachment to a support (not shown). In this embodiment the working area consists of three flutes 2a, 2b, and 2c wound around a central axis, the edges 4a, 4b and 4c of which are positioned on a conical envelope 5 that narrows in section from the extremity near supporting tip 2 to the point 6 of instrument 1. Flutes 2a, 2b and 2c all comprise rectilinear segments S, defined, for example, between transverse cross-section lines 1C-1C and 1D-1D in FIG. 1A.

FIGS. 1C and 1D correspond respectively to the transverse cross-sections of the instrument at the level of cross-section lines 1C-1C and 1 D-1 D. It will be noted that edges 4a, 4b, and 4c of flutes 2a, 2b and 2c are always positioned on conical envelope 5 of working area 2 on instrument 1. It is this feature that characterizes the instrument.

With reference to FIGS. 2A, 2B, 2C and 2D, instrument 101 such as the one shown for drilling root canals in a patient's tooth corresponding to the prior art defined in French Patent No. 01 02452 comprises a working area 102 designed to form and/or shape and/or cut the interior wall of the root canal, the working area being equipped with a supporting tip 103 designed for attachment to a support (not shown). In this embodiment, the working area consists of three flutes 102a, 102b and 102c wound around a central axis, the edges 104a, 104b and 104c of which are positioned either on a conical envelope 105 that narrows in section from the extremity near supporting tip 103 to point 106 of instrument 101, or inside the envelope. Flutes 102a, 102b and 102c all comprise continuously curved sections that are illustrated in the enlarged view of FIG. 2B.

FIGS. 2C and 2D correspond respectively to the transverse cross-sections of the instrument at the level of lines 2D-2D and 2D-2D. It will be noted that edges 104a, 104b and 104c of flutes 102a, 102b and 102c are positioned on conical envelope 105 of working area 102 on instrument 101 at the location of transverse cross-section 2C-2C and inside this conical envelope 105 at the location of transverse cross-section 2D-2D. It is this feature that characterizes this instrument.

FIGS. 3A, 3B, 3C, 3D, 3E and 3F illustrate an instrument 20 according to the invention that comprises, like the instruments described below, a working area 21 designed to form and/or shape and/or cut the interior wall of the root canal, the working area being equipped with a supporting tip 23 designed for attachment to a support (not shown). This instrument may be displaced rotationally during use, driven by a mechanical hand piece, or axially in a back and forth motion. Working zone 21 may consist of three flutes 22a, 22b and 22c or four flutes 22'a, 22'b, 22'c and 22'd wound around a central axis, the edges 24a, 24b and 24c or 24'a, 24'b, 24'c and 24'd are either positioned on a conical envelope 25 that narrows from the extremity near supporting tip 23 to point 26 of instrument 20, or positioned inside the envelope 25.

The flutes, either three in number or four as shown in cross-sections along lines 3C-3C, 3D-3D and 3E-3E, 3F-3F in FIGS. 3C, 3E and 3D, 3F are wound around a central axis of instrument 20 and their edges are positioned either on conical envelope 25 or inside this conical envelope 25. In actuality, in the active sections for cutting and drilling the root canal, the edges are positioned on conical envelope 25; whereas in the sections for evacuating the cut material through the active sections, the edges are positioned inside this conical envelope 25.

FIG. 3B illustrates an enlarged view of a portion of the working zone 21. Views 3C and 3E correspond to the cross-sections of two variations of instrument 20 along transverse line 3C-3C, 3E-3E. In one instance, the instrument comprises three flutes and in the other, it comprises four flutes. The views in FIGS. 3D and 3F correspond to the cross-sectional views of these two variations of instrument 20 along transverse line 3D-3D, 3F-3F.

Working area 21 is actually subdivided into segments S in which alternate flutes have a straight section S1 and a twisted spiral section S2 arranged in such a way that their edges are located either on the conical envelope or inside the conical envelope at the level of straight sections S1 or at the level of twisted sections S2.

As FIGS. 3A and 3B show more specifically, each segment S of the three flutes 22a, 22b and 22c or the four flutes 22'a, 22'b, 22'c and 22'd comprises some straight sections S1 and some twisted spiral sections S2 that extend alternately from one another. Each segment comprises one straight section and one twisted segment. Edges 24a, 24b and 24c of flutes 22a, 22b and 22c at the level of line 3D-3D, 3F-3F on the straight sections are positioned inside conical envelope 25, as shown in FIG. 3D, such that their transverse section is smaller than that of the twisted sections, called the active sections, the edges of which are positioned on conical envelope 25 as shown in FIG. 3C. The latter shows the cross-sectional view of working area 21 at the level of cross section A-A. The smaller straight sections efficiently evacuate the material removed from the root canal walls while it is being shaped with the twisted sections which in this case are known as the active sections. This geometry corresponds to a first embodiment of the instrument of the invention.

A variation of the instrument of the invention is illustrated by FIGS. 3E and 3F representing cross-sections at the level of lines 3E-3E and 3F-3F, respectively, of working area 21 comprising four flutes 22'a, 22'b, 22'c and 22'd. The results are identical to those that occur with segments comprising three flutes.

FIGS. 4A, 4B, 4C and 4D illustrate an instrument 30 according to the invention that comprises, like the instruments described below, a working area 31 designed to form and/or shape and/or cut the interior wall of the root canal, the working zone being equipped with a supporting tip 33 designed for attachment to a support (not shown). This instrument may be used using rotational displacement, driven by a mechanical hand piece, or using axial back and forth movement. The working zone may consist of three flutes 32a, 32b and 32c wrapped around a central axis, the edges 34a, 34b and 34c of which are either positioned on a conical envelope 35 that narrows in section from the extremity near supporting tip 33 to point 36 of instrument 30, or positioned inside the envelope. The flutes, three in number (or perhaps four), as shown in cross-section along lines 4C-4C and 4D-4D of FIGS. 4C and 4D are twisted and their edges are positioned either on conical envelope 35 or inside this conical envelope 35. Working area 31, one enlarged portion of which is illustrated in FIG. 4B, is actually subdivided into segments S, the flutes 32a, 32b and 32c of which are alternately straight in section S1 and twisted in section S2. The flutes are arranged so their edges 34a, 34b, 34c are located either inside the conical envelope 35 at the level of straight sections S1, or on the conical envelope 35 at the level of twisted sections S2.

Generally speaking, the endodontic instrument is made in such a way that the number of segments (S) ranges from one to five. In addition, the transverse section of the instrument in the portions where the edges are located on the conical envelope (25; 35) and the portions where the edges (24a, 24b, 24c; 34a, 34b, 34c) are located inside the conical envelope has a surface difference ranging from 5 to 50%. This surface reduction in the areas where the edges are inside the envelope must be below the fragility threshold of the instrument, but nevertheless sufficient to facilitate the evacuation of material.

In fact, in each segment, the active sections for cutting and drilling the root canal comprise a straight segment S that is positioned on conical envelope 35, while in the sections for evacuating cut material through the active sections, the edges are positioned inside the envelope 35.

The present invention is not limited to the embodiments described, but may undergo various modifications or variations obvious to a person skilled in the art.

The invention claimed is:

1. An endodontic instrument (20; 30) for drilling a tooth of a patient, the instrument having a longitudinal axis and comprising:
   a working area (21; 31),
   the working area being designed to at least one of form, shape and cut an interior wail of a root canal,
   the working area having a first extremity (26; 36) and a second extremity attached to a supporting tip (23; 33) which is designed for attachment to a support,
   the working area (21; 31) comprising several flutes (22a, 22b, 22c; 32a, 32b, 32c) wound in a spiral around a central axis inside a conical envelope (25; 35) that narrows in section from the second extremity to the first extremity of the instrument,
   the working area (21; 31) being subdivided into axially adjacent longitudinal segments (S) in which the flutes alternately have a straight section (S1) extending along the longitudinal axis and a twisted spiral section (S2) extending along the longitudinal axis,
   the edges (24a, 24b, 24c; 24'a, 24'b, 24'c, 24'd) of the flutes (22a, 22b, 22c; 22'a, 22'b, 22'c, 22'd) of each straight section (S1) of each longitudinal segment (S) is situated inside the conical envelope (25), and
   the edges (24a, 24b, 24c; 24'a, 24'b, 24'c, 24'd) of the flutes (22a, 22b, 22c; 22'a, 22'b, 22'c, 22'd) of each twisted spiral section (S2) of each longitudinal segment (S) located on the conical envelope (25).

2. The endodontic instrument according to claim 1, wherein the working area (21; 31) comprises at least two flutes.

3. The endodontic instrument according to claim 1, wherein, for each of the axially adjacent segments (S), a cross sectional surface area of the flutes at the level of the straight section (S1) of the working area (31), has a lower surface area than a cross sectional surface area of the flutes at the level of the axially adjacent twisted spiral section (S2) of the working area.

4. The endodontic instrument according to claim 1, wherein, for each of the axially adjacent longitudinal segments (S), a transverse section of the working area (21; 31), at the level of the straight section (S1) and, at the level of the twisted spiral section (S2), forms an equilateral triangle centered on the central axis.

5. The endodontic instrument according to claim 1, wherein, for each of the axially adjacent longitudinal segments (S), a transverse section of the working area (21), at the level of the straight section (S1), and, at the level of the twisted spiral section (S2), forms a square centered on the central axis.

6. An endodontic instrument for drilling a tooth of a patient, the instrument having a longitudinal axis and comprising:
- a working area having first and second ends and the working area being in a form of a conical envelope that narrows from the second end to the first end, the second end of the working area being connected to a supporting tip and the first end of the working area being remote from the second end of the working area;
- the working area being designed to at least one of form, shape and cut an interior wall of a root canal;
- the working area comprising a plurality of flutes that extend axially from the first end to the second end thereof, the plurality of flutes being wound in a spiral along the longitudinal axis, the plurality of flutes being connected such that adjacent flutes form an edge;
- the plurality of flutes being subdivided into axially extending straight sections and axially extending twisted spiral sections, the straight sections of the flutes and the twisted spiral sections of the flutes are axially alternately arranged along the longitudinal axis from the first end of the working area to the second end of the working area;
- along one of either the straight sections or the twisted spiral sections of the flutes, the edges of the flutes are radially located on a perimeter of a cross section of the conical envelope; and
- along the other one of either the twisted spiral sections or the straight sections of the flutes, the edges of the flutes are located radially within and spaced from the perimeter of the cross section of the conical envelope.

* * * * *